US 7,227,122 B2

(12) United States Patent
Arai

(10) Patent No.: US 7,227,122 B2
(45) Date of Patent: Jun. 5, 2007

(54) IMAGE PROCESSING APPARATUS AND METHOD FOR PROCESSING IMAGES

(75) Inventor: Satoshi Arai, Hachioji (JP)

(73) Assignee: Olympus Corporation, Tokyo (JP)

( * ) Notice: Subject to any disclaimer, the term of this patent is extended or adjusted under 35 U.S.C. 154(b) by 222 days.

(21) Appl. No.: 10/955,782

(22) Filed: Sep. 30, 2004

(65) Prior Publication Data
US 2005/0073685 A1    Apr. 7, 2005

(30) Foreign Application Priority Data
Oct. 3, 2003  (JP) ............................. 2003-345997

(51) Int. Cl.
*G01J 3/50* (2006.01)
*H01J 40/14* (2006.01)
*H01J 5/16* (2006.01)
*G01N 21/00* (2006.01)
*G01N 15/06* (2006.01)

(52) U.S. Cl. .................. 250/226; 356/418; 250/338.5; 250/573

(58) Field of Classification Search ................ 250/226, 250/573, 339.01, 339.07, 338.5; 356/402–425
See application file for complete search history.

(56) References Cited

U.S. PATENT DOCUMENTS

| 5,717,605 A | 2/1998 | Komiya et al. |
| 5,986,767 A * | 11/1999 | Nakano et al. ............ 356/419 |
| 6,721,459 B1 | 4/2004 | Honsinger et al. |
| 6,856,390 B2 * | 2/2005 | Nordman et al. ........... 356/344 |

FOREIGN PATENT DOCUMENTS

| JP | 1-313735 A | 12/1989 |
| JP | 4-104243 A | 4/1992 |
| JP | 2001-188903 A | 7/2001 |
| JP | 2002-71552 A | 3/2002 |
| JP | 2002-139424 A | 5/2002 |
| JP | 2003-57178 A | 2/2003 |
| JP | 2003-65948 A | 3/2003 |
| WO | WO 99/16353 A1 | 4/1999 |

OTHER PUBLICATIONS

"Optics Communications" vol. 188, No. 1-4, pp. 47-54, ISSN: 0030-4018, Publ. Elsevier Science B.V., Feb. 1, 2001.
K. Fujii et al; "Analysis of Tissue Samples Using Transmittance Spectra—The Method of Considering the Differences of Dyeing Conditions"; Third Color Symposium for Digital Biological Medical Images Standardization of Pathologic Diagnosis and Precision Management Medicine and Progress; vol. 176, No. 10, Mar. 1996.
Y. Murakami et al; "Spectral Reflectance Estimation from Multi-Band Image Using Color Chart"; Optics Communications 188, 2001; pp. 47-54.

* cited by examiner

*Primary Examiner*—Georgia Epps
*Assistant Examiner*—Patrick J. Lee
(74) *Attorney, Agent, or Firm*—Frishauf, Holtz, Goodman & Chick, P.C.

(57) ABSTRACT

An image processing apparatus uses a camera to pick up images of an image pickup target illuminated by a transmission type illumination, via optical filters, and then allows a spectral characteristic estimating section and a pigment amount estimating section to calculate a physical amount relating to the image pickup target for each pixel of the image pickup target, on the basis of the picked-up multiple band images. On this occasion, the image processing apparatus uses the optical filters the number of which is equal to the number of independent components of the calculated physical amount.

17 Claims, 5 Drawing Sheets

IMAGE PROCESSING APPARATUS AND METHOD FOR PROCESSING IMAGES

CROSS-REFERENCE TO RELATED APPLICATIONS

This application is based upon and claims the benefit of priority from prior Japanese Patent Application No. 2003-345997, filed Oct. 3, 2003, the entire contents of which are incorporated herein by reference.

BACKGROUND OF THE INVENTION

1. Field of the Invention

The present invention relates to an apparatus and method for processing images which uses an optical filter to evaluate physical characteristics of an object.

2. Description of the Related Art

In the prior art, to pick up an image for image processing, an RGB camera is used to acquire color information. The color information acquired using the RGB camera is similar to human visual information and is thus characterized by being readily understood by human beings.

However, the color information is subjective information having an intermediate position in a human visual recognition process. It is thus difficult to make this information physically objective. That is, the human recognition of colors varies depending on an observation environment or a physical state. The recognition cannot be easily quantified or normalized. Thus, for example, if any lesion in a tissue sample is to be recognized, it is difficult to form a criterion.

In contrast, the spectral characteristic (hereinafter referred to as a spectrum) of a target is a physical characteristic inherent in the target and can be quantified as an objective value not affected by human subjectivity. A characteristic amount derived from the spectrum can be used as a criterion for objective determinations. A spectral image is obtained by acquiring spectral data on a target for each pixel and arranging the spectral data in image form. The spectral image contains important physical information on the target.

Much attention has long been paid to image processing using a spectrum. Various attempts have been made particularly in the field of diagnostic support.

For example, WO99/16353 discloses a method of diagnosing spectral biological image of eye which method comprises using an interferometer to divide light emitted to and reflected by the fundus of the eye and processing the resulting spectrum to recognize the concentration of hemoglobin in the retina blood vessels.

Further, other techniques for spectral processing include "Analysis of tissue samples using transmittance spectra— The method of considering the differences of dyeing conditions" (Fujii et al., Third "Color" Symposium for Digital Biological Medical Images). With this technique, the amounts of dyeing pigments contained in a pathological sample is estimated as a two-dimensional map on the basis of the spectral transmittance of the sample and the transmittances of the dyeing elements.

BRIEF SUMMARY OF THE INVENTION

According to a first aspect of the present invention, there is provided an image processing apparatus comprising:

image pickup section configured to use an image pickup element to pick up images of a target illuminated by a transmission type illumination, via optical filters; and calculating section configured to calculate a physical amount relating to the target for each pixel of the target on the basis of the images picked up by the image pickup section, the number of optical filters used for the image pickup being equal to the number of independent components of the physical amount calculated by the calculating section.

According to a second aspect of the present invention, there is provided a method for processing images, the method comprising:

picking up images of a target illuminated by a transmission type illumination, via optical filters; and calculating a physical amount relating to the target for each pixel of the target on the basis of the picked-up images, the number of optical filters used for the image pickup being equal to the number of independent components of the calculated physical amount.

According to a third aspect of the present invention, there is provided a method for processing images, the method comprising:

picking up images of a target dyed with a plurality of predetermined pigments, via a plurality of optical filters with different spectral characteristics;

calculating and estimating the amount of each of the plurality of pigments relating to the target for each pixel of the target on the basis of the picked-up images; and analyzing the target on the basis of a distribution of the estimated amounts of the pigments, the number of the plurality of optical filters being equal to the number of independent components of the calculated and estimated amounts of pigments, and a combination of the different spectral characteristics of the plurality of optical filters being preselected so as to minimize errors in estimation of the calculated and estimated amounts of pigments.

According to a fourth aspect of the present invention, there is provided an image processing apparatus comprising:

image pickup means for using an image pickup element to pick up images of a target illuminated by a transmission type illumination, via optical filters; and calculating means for calculating a physical amount relating to the target for each pixel of the target on the basis of the images picked up by the image pickup means, the number of optical filters used for the image pickup being equal to the number of independent components of the physical amount calculated by the calculating means.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The embodiments of the present invention will be explained with reference to the accompanying drawings.

First Embodiments

According to the present embodiment, a transmission type illumination is used to take images of a translucent object containing pigments so that the images cover multiple bands. Then, a spectral transmittance of each pixel of the image is estimated. Moreover, the amount of respective pigment contained in each pixel is estimated on the basis of the spectral transmittance.

In the present embodiment, the translucent object is assumed to be a pathological tissue sample. The pigments are assumed to be hematoxylin and eosin. That is, a physical amount to be finally obtained is the amounts of the pigments hematoxylin and eosin. The number of independent components is "2".

Figure 1:
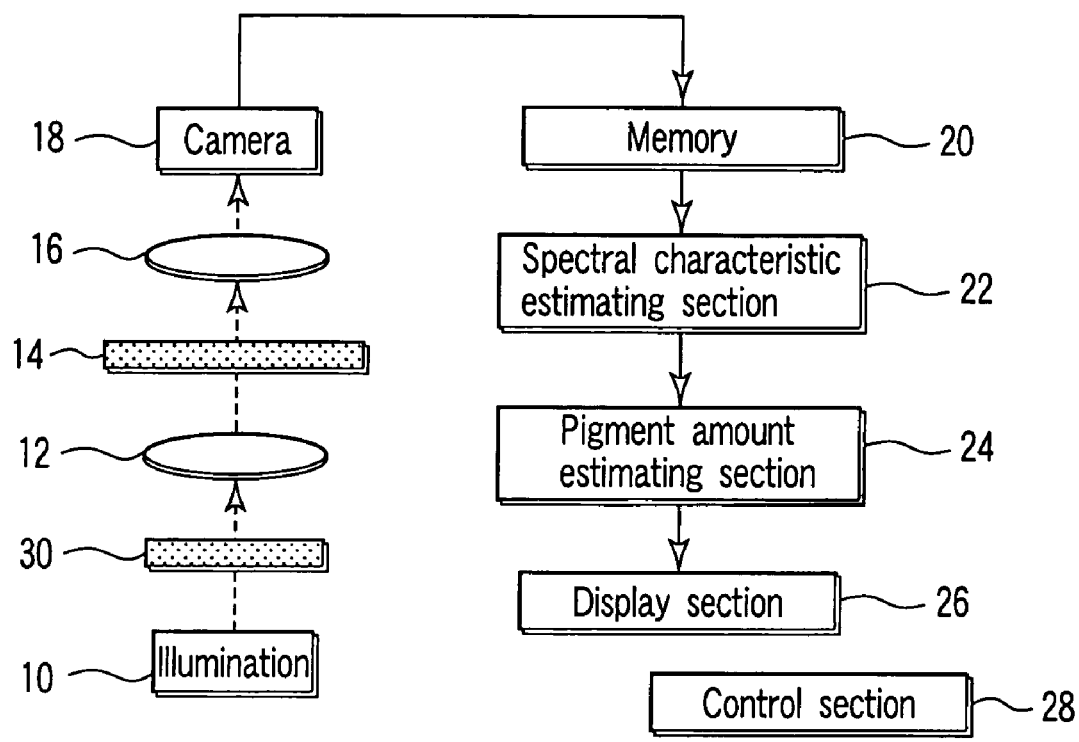
FIG. 1 is a diagram showing a configuration of an image processing apparatus according to a first embodiment of the present invention.

The image processing apparatus according to the present embodiment is composed of an illumination 10, an objective optical system 12, optical filters 14, an image forming optical system 16, a camera 18, a memory 20, a spectral characteristic estimating section 22, a pigment amount estimating section 24, a display section 26, and a control section 28 as shown in FIG. 1. However, the connection between the control section 28 and each section of the apparatus is not shown for simplification of the drawing.

Figure 2:
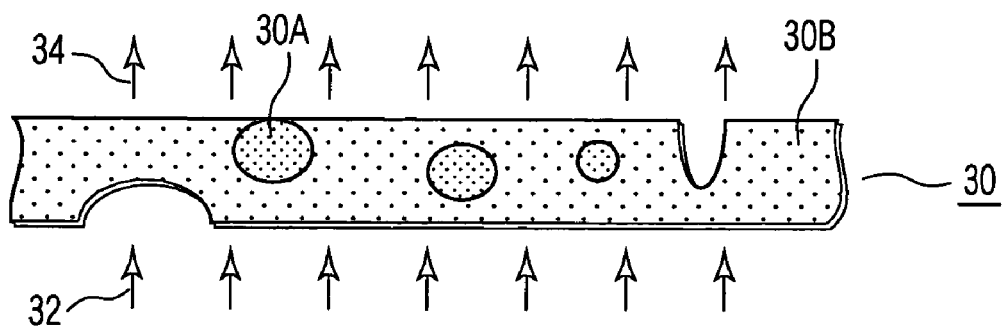
FIG. 2 is a diagram showing a section of a dyed tissue sample.

In the image processing apparatus according to the present embodiment, an image pickup target 30 is installed on a stage (not shown). Then, the image pickup target 30 is irradiated with light (incident light 32) from the illumination 10, located opposite the camera 18, as shown in FIG. 2. In FIG. 2, reference numeral 30A denotes a region (mainly a cell nucleus) dyed with hematoxylin. Reference numeral 30B denotes a region (mainly a cytoplasm) dyed with eosin. The light transmitted through the image pickup target 30 (transmitted light 34) is formed by the objective optical system 12 and image forming optical system 16 into an image on an image pickup surface of an image pickup element (not shown) provided in the camera 18. Moreover, one of the optical filters 14, each having a larger diameter than a luminous flux at least at that time, is placed on any point on the optical path extending from the illumination 10 to the image pickup surface of the camera 18. In this case, the optical filters 14 are configured to be changeable, and the number of optical filters 14 is the same as that of independent components of the physical amount to be finally obtained. Specifically, the number of optical filters 14 is two. With this configuration, multiple band images can be picked up by performing a change of the optical filters 14 and an image pickup operation sequentially or in parallel. In the present embodiment, an image for two bands can be obtained for each pixel. Multiple band images (two band images) thus picked up are then stored in the memory 20.

In the configuration in FIG. 1, the optical filters 14 are arranged between the objective optical system 12 and the image forming optical system 16. However, the present invention is not limited to this arrangement. For example, a configuration is applicable in which the changeable optical filters 14 and the camera 18 are integrated together so that the filters can be changed using a turret, as disclosed in U.S. Pat. No. 5,717,605.

Figure 3:
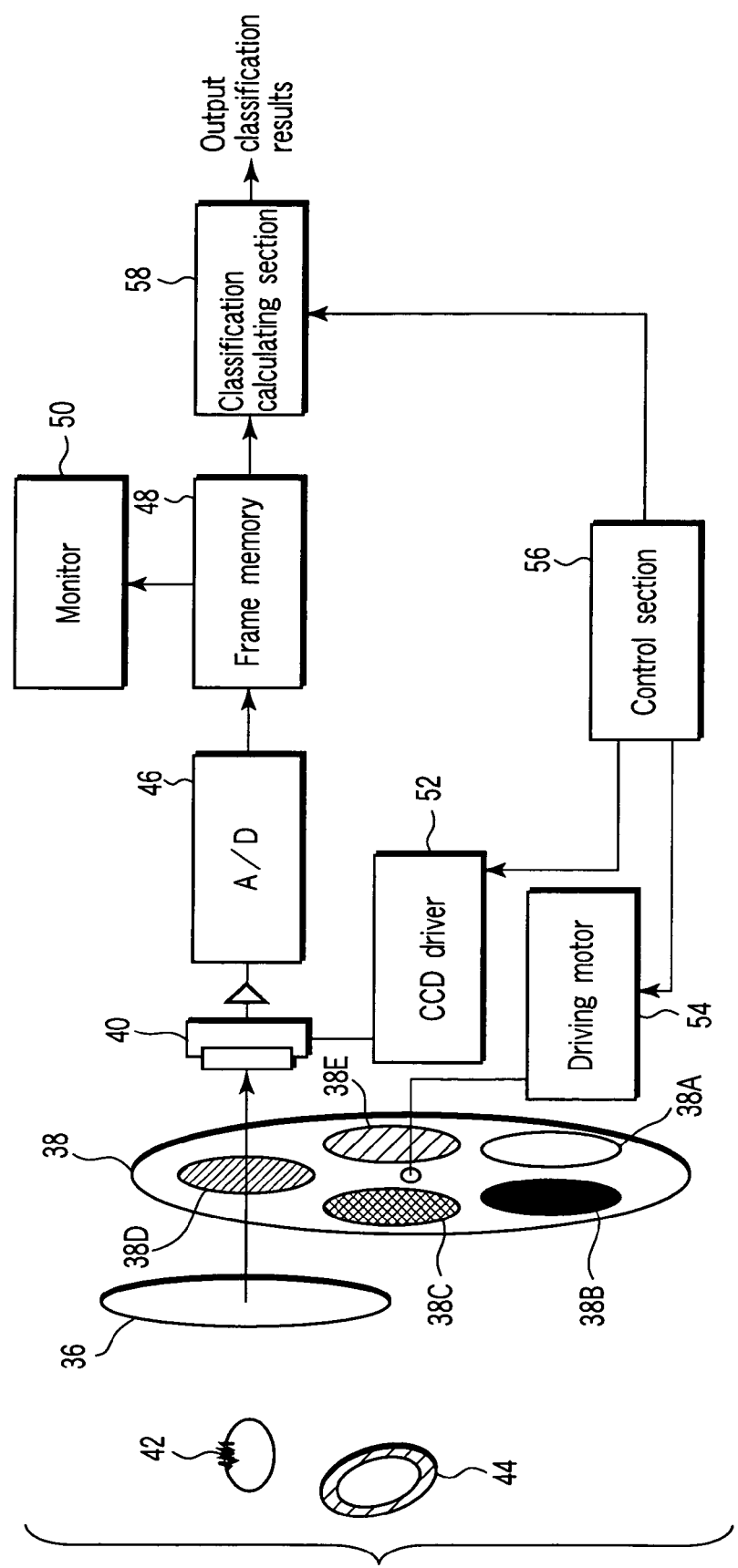
FIG. 3 is a diagram showing a configuration of a conventional color classifying device as an example of an image pickup device for multiple band images.
Figure 4A:
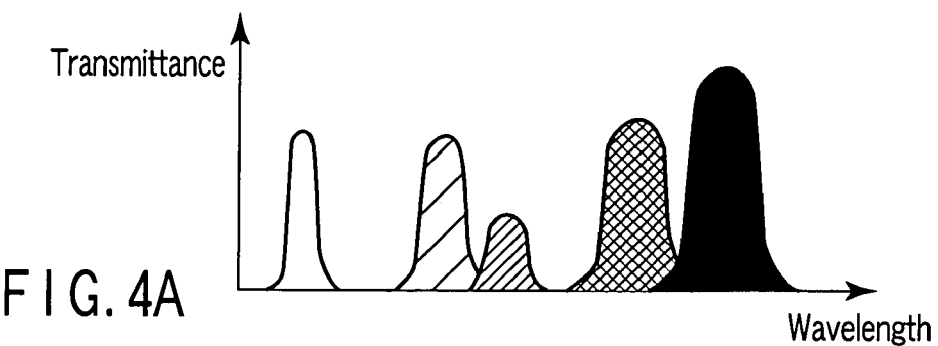
FIG. 4A is a graph showing the characteristics of multiple band pass filters used in a rotary color filter used in the color classifying device in FIG. 3.
Figure 4B:
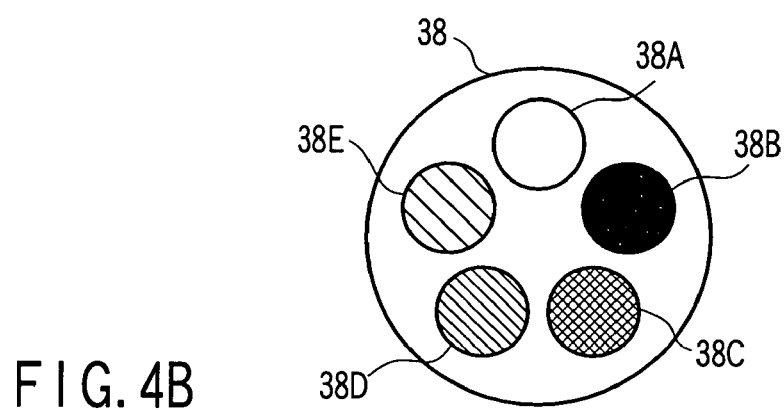
FIG. 4B is a diagram showing a configuration of the rotary color filter.
Figure 4C:
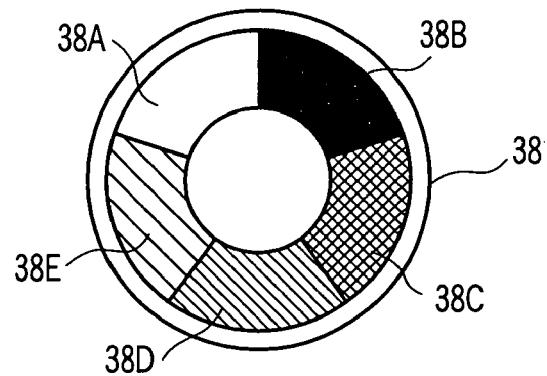
FIG. 4C is a diagram showing another configuration of the rotary color filter.

As shown in FIG. 3, the color classifying device disclosed in U.S. Pat. No. 5,717,605 is composed of: an optical system 36 including a diaphragm or a lens; a rotary color filter 38 composed of a plurality of band pass filters 38A, 38B, . . . , 38E having such characteristics as shown in FIG. 4A; a CCD 40 that loads images of a target 42 and a reference plate 44; an A/D converter 46; a frame memory 48; a monitor 50 that displays a part being photographed; a CCD driver 52; a driving motor 54 for the rotary color filter 38; a control section 56 which controls the CCD driver 53, the rotary color filter driving motor 54, and the like and which sends instructions to a classification calculating section 58; and the classification calculating section 58 that carries out classification. The rotary color filter 38 is composed of the band pass filters 38A to 38E, which are of a number of types, as shown in FIG. 4B or FIG. 4C. The filters are thus characterized by allowing respective arbitrary band widths to be transmitted as shown in FIG. 4A. In FIG. 4B or FIG. 4C, the rotary color filter 38 is composed of five band pass filters. The above U.S. patent states that the optical system 36 and the rotary color filter 38 may be inversely arranged, that is, the rotary color filter 38 may be placed in front of the optical system 36.

Thus, the above USP discloses the color classifying device, but its arrangement for changing the filters is applicable to the present embodiment. Of course, the present embodiment does not require five filters but only two.

Figure 5:
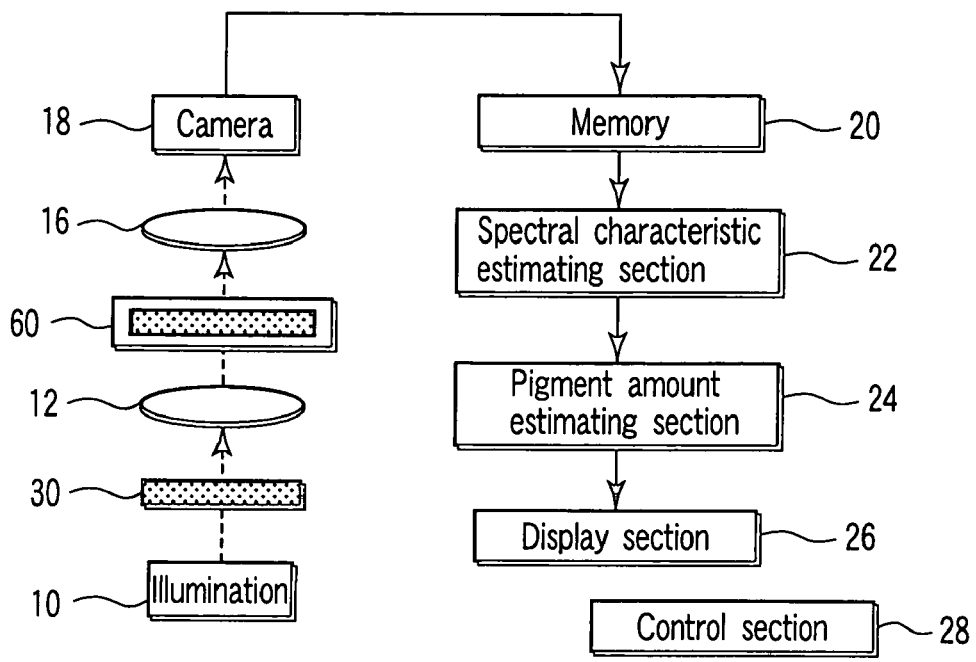
FIG. 5 is a diagram showing a variation of the image processing apparatus according to the first embodiment.
Figure 6:
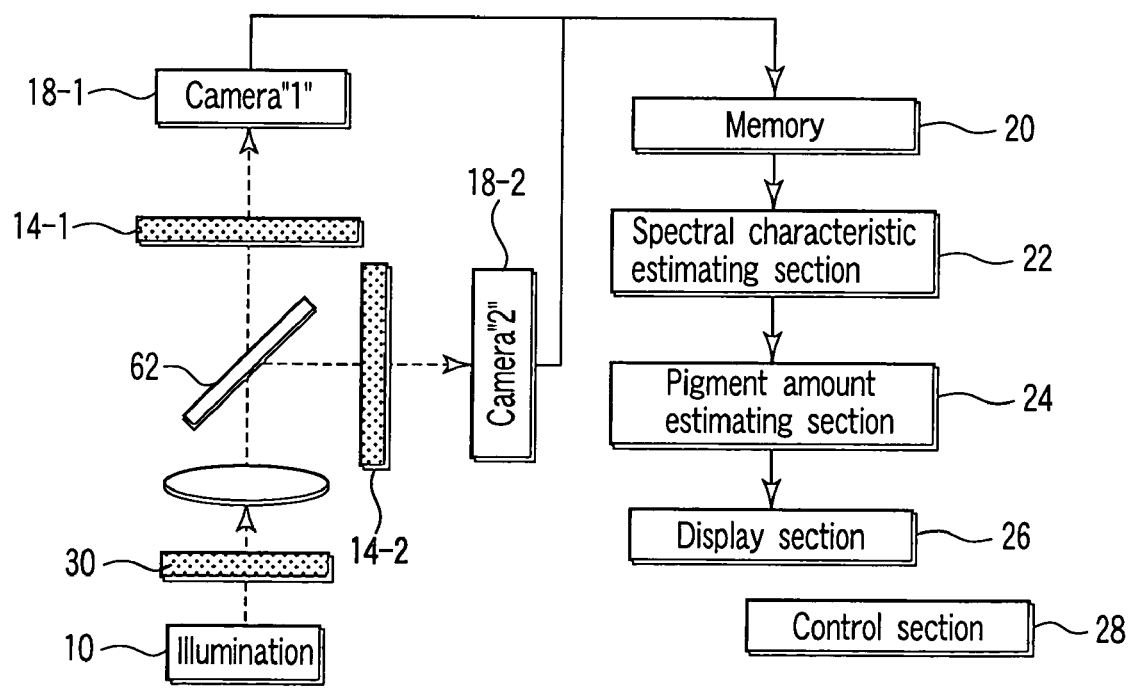
FIG. 6 is a diagram showing another variation of the image processing apparatus according to the first embodiment.

Further, a transmission wavelength variable optical filter 60 may be used as shown in FIG. 5 instead of changing the physically different optical filters 14 with each other. Alternatively, as shown in FIG. 6, a half mirror 62 or the like may be used to divide the optical path into pieces in accordance with the number of optical filters so that as many cameras 18 (a camera "1" 18-1 and a camera "2" 18-2) as the optical filters 14 (an optical filter "1" 14-1 and an optical filter "2" 14-2) can simultaneously take images.

For the optical filters 14 and the camera 18, any arrangement can be used to acquire multiple band images of the target. However, the position of the image of the target on the image pickup surface of the image pickup element of the camera 18 must be stationary during an image taking period.

Once multiple band images are accumulated in the memory 20, the spectral characteristic estimating section 22 determines the spectral transmittance of the target for each pixel on the basis of the multiple band images. This process is, for example, the technique disclosed in "Spectral reflectance estimation from multi-band image using color chart"

(Murakami et al., Optics Communications 188 (2001), 47–54) and which is applied to the observation of transmission through a translucent object.

According to the technique disclosed in this document, the spectral transmittance $\hat{t}(x, y)$ of the image pickup target 30 can be estimated, by the Wiener estimation, on the basis of a value g(x, y) for a pixel picked up at a position (x, y) using the spectral transmittance of the optical filters 14, the spectral characteristic of the illumination 10, the spectral sensitivity of the camera 18, the correlation matrix of spectral transmittance of the image pickup target 30, and the correlation matrix of image pickup noise.

In this connection, it is necessary to match a wavelength range, a wavelength sampling interval, and a wavelength sampling number with one another at the spectral transmittance of the optical filters 14, the spectral characteristic of the illumination 10, and the spectral sensitivity of the camera 18. The wavelength range, the wavelength sampling interval, and the wavelength sampling number are subsequently used in the Wiener estimation. Consequently, estimation can be carried out at an arbitrary wavelength resolution by controlling data provided as a spectral characteristic.

In the present embodiment, the wavelength range is a visible light area, and the wavelength sampling number is at least "three".

The spectral transmittance of the image pickup target 30 can be determined for all the pixels subjected to multi-band image pickup by defining each pixel of multiple band images as g(x, y) and executing an estimation process while sequentially moving the pixels.

Since the spectral transmittance of the image pickup target 30 is used to calculate a Wiener estimation matrix, the estimated value is obtained in the form of a spectral transmittance. It is thus unnecessary to execute a process of normalizing the estimated value using the characteristics of the illumination 10.

Further, since the noise characteristic of the image pickup element is incorporated into conditions for the Wiener estimation, the optimum result of estimation is obtained which takes an SN ratio into account.

Then, the pigment amount estimating section 24 determines the amounts of pigments in the image pickup target 30 for each pixel on the basis of the result of estimation of the spectral transmittance by the spectral characteristic estimating section 22. This process employs the technique disclosed in the document of Fujii et al. "Analysis of tissue samples using transmittance spectra—The method of considering the differences of dyeing conditions".

According to the technique disclosed in the document of Fujii et al., the spectral transmittance of hematoxylin and the spectral transmittance of eosin can be used to estimate, through the application of the Lambert-Beer's law, the two-dimensional distribution $C_h(x, y)$ of the amount of hematoxylin pigment and the two-dimensional distribution $C_e(x, y)$ of eosin pigment on the basis of the two-dimensional distribution $I(\lambda, x, y)$ of spectral transmittance of the image pickup target 30 at the position (x, y) determined by the spectral characteristic estimating section 22.

After dyeing with hematoxylin and eosin, most of the hematoxylin pigment is present inside the cell nucleus. Consequently, the distribution $C_h(x, y)$ of the amount of hematoxylin pigment can be considered to the distribution of cell nuclei. Further, most of the eosin pigment is present inside the cytoplasm. Consequently, the distribution $C_e(x, y)$ of the amount of eosin pigment can be considered to the distribution of cytoplasms.

The thus estimated distributions of amounts of pigments are displayed on the display section 26.

With at least two optical filters 14, used for the above process, the amounts of pigments can be estimated because the number of independent components that determine the spectral transmittance of the image pickup target 30, that is, the number of pigments, is "2". Moreover, the spectral characteristic can be selected so as to minimize errors in the estimated amounts of pigments. This may be accomplished by, for example, providing multiple band pass filters having different central wavelengths and different full widths at half maximum and searching for a combination of band pass filters which minimizes errors in the estimation of the amounts of pigments.

Since the noise characteristic of the image pickup element is used during the Wiener estimation, the condition for the noise characteristic of the image pickup element is naturally contained in the spectral characteristic of the image pickup target 30 resulting from the Wiener estimation and in the amounts of pigments based on the spectral characteristic of the image pickup target 30. Accordingly, the selection of the optimum filter reflects the condition for the minimization of errors in the amounts of pigments but also the condition for the noise characteristic of the image pickup element.

The above described processing makes it possible to take multiple band images of a pathological tissue sample, determine the spectral transmittance for each pixel, and two-dimensionally determine the amounts of pigments, corresponding to the physical amount. The amounts of the pigments hematoxylin and eosin have strong correlations with the distribution of presences in the tissue and thus provide beneficial information for the analysis of the tissue sample. On the other hand, the present embodiment uses only two optical filters 14, it is thus only necessary to take two band images. Therefore, this technique includes the spectral processing but can reduce the time for image taking and transmission to significantly reduce the storage capacity and the time for processing.

Second Embodiments

The present embodiment further improves the multi-band image pickup section in the first embodiment to eliminate the need for a mechanically driven change of the filter or image taking based on the division of the optical path.

In the present embodiment, the translucent object is assumed to be a pathological tissue sample. The pigments are assumed to be hematoxylin and eosin. That is, a physical amount to be finally obtained is the amounts of the pigments hematoxylin and eosin. The number of independent components is "2".

Figure 7:
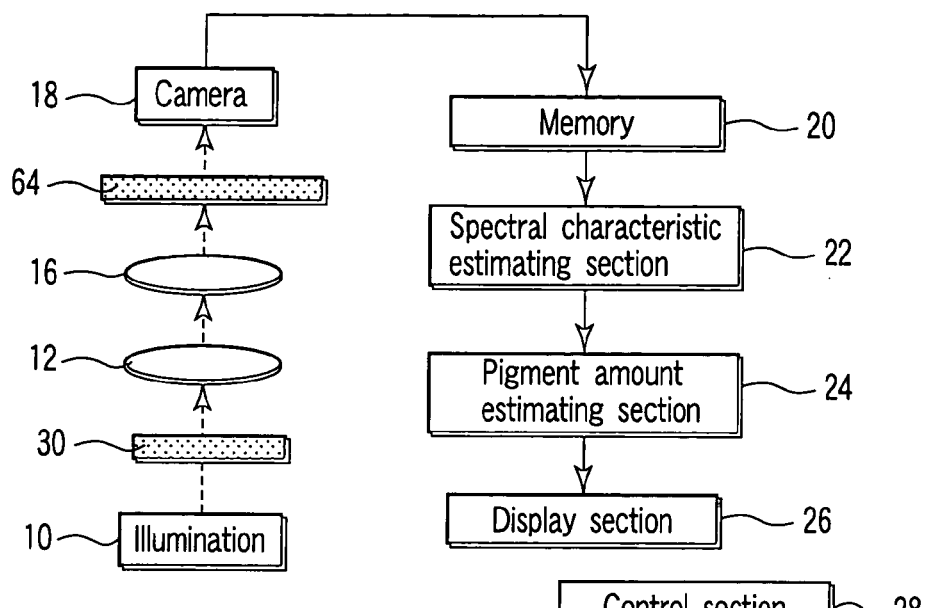
FIG. 7 is a diagram showing a configuration of an image processing apparatus according to a second embodiment of the present invention.

FIG. 7 is a diagram showing a configuration of an image processing apparatus according to the present embodiment. However, the connection between the control section 28 and each section of the apparatus is not shown for simplification of the drawing. The following description will be given with reference to FIG. 7.

Figure 8:
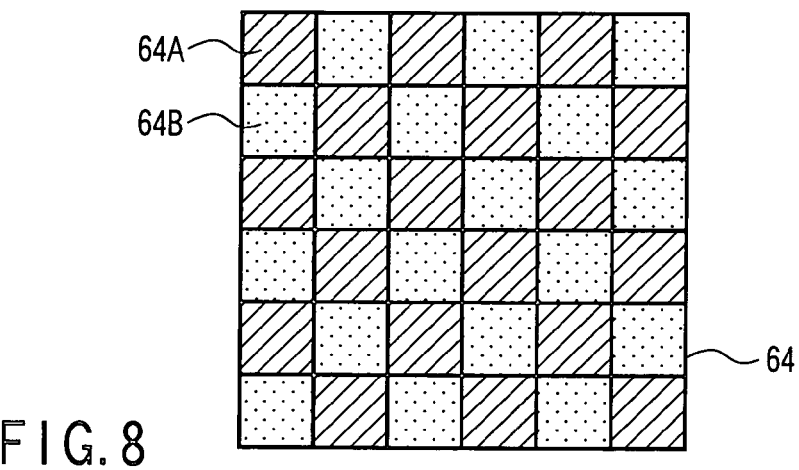
FIG. 8 is a diagram showing an optical filter configured like a lattice.

As in the case of the first embodiment, the image pickup target 30 installed on the stage is irradiated with light from the illumination 10, located opposite the camera 18. The transmitted light is formed by the objective optical system 12 and image forming optical system 16 into an image on the image pickup surface of the image pickup element of the camera 18. In the present embodiment, an optical filter 64 having the appearance shown in FIG. 8 is placed on the image pickup surface of the camera 18 or at an optically conjugate position of the image pickup surface. The optical filter 64 is composed of sections of materials 64A and 64B having different spectral characteristics and covering the filter in a checkered pattern. The position of the optical filter 64 is adjusted so that the sections of the filter correspond to the respective pixels.

Figure 9:
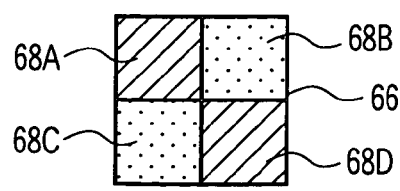
FIG. 9 is a diagram showing a local image area.

With this configuration, a one-band image is taken. The spectral characteristic and the amounts of pigments are calculated from the taken image as in the case of the first embodiment. However, in the present embodiment, an image for only one band is obtained for a single pixel. Thus, a set of proximate pixels such as the one shown in FIG. 9 is considered to be one local image area 66. The spectral characteristic estimating section 22 then obtains a pixel value for two bands by executing the processing described below:

(1) An average pixel value for pixels 68A and 68D is calculated as a pixel value for a first band at the position of the local image area 66;

(2) An average pixel value for pixels 68B and 68C is calculated as a pixel value for a second band at the position of the local image area 66; and These processes are executed for each local image area 66.

In this case, an effective pixel resolution decreases to half but an image for two bands can be taken using an image pickup element made of a single plate. A false two-band image thus obtained can sufficiently accurately approximate a true two-band image provided that its pixel resolution is high.

Then, the spectral characteristic estimating section 22 uses the same procedure that used in the first embodiment to estimate the spectral characteristic. However, the spectral transmittance is not calculated for each pixel but for each local image area 66.

Moreover, the pigment amount estimating section 24 uses the same procedure that used in the first embodiment to estimate the amounts of pigments. However, the amounts of pigments are not calculated for each pixel but for each local image area 66.

The above described processing makes it possible to take a multi-band image using the image pickup element made of a single plate, determine the spectral transmittance for each set of proximate pixels, and two-dimensionally determine the amounts of pigments, corresponding to the physical amount. In spite of a decrease in effective resolution, it is not difficult to obtain information on a practical resolution in view of the large number of pixels used in the recent CCD or CMOS image pickup element. In the present embodiment, only one image is taken, so that a data capacity is much smaller than that in the first embodiment. As in the case of the first embodiment, this technique includes the spectral processing but can reduce the time for image taking and transmission to significantly reduce the storage capacity and the time for processing.

The first embodiment and the present embodiment are effective when appropriate modes are selected for them in accordance with the desired resolution and data capacity.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An image processing apparatus comprising:
   an image pickup section configured to use an image pickup element to pick up images of a target illuminated by transmission type illumination, via a number of optical filters;
   a spectral characteristic estimating section configured to estimate a spectral characteristic relating to the target for a plurality of pixels of the target based on the images picked up by the image pickup section; and
   a pigment amount estimating section configured to estimate an amount of a number of pigments relating to each of the plurality of pixels of the target based on the spectral characteristic;
   wherein the number of optical filters used for the image pickup is equal to the number of pigments whose amount is estimated by the pigment amount estimating section.

2. The image processing apparatus according to claim 1, wherein the optical filters are selected in accordance with conditions relating to minimization of errors in estimating by the pigment amount estimating section.

3. The image processing apparatus according to claim 2, wherein the conditions include a combination of spectral characteristics which minimizes errors in estimating by the pigment amount estimating section.

4. The image processing apparatus according to claim 2, wherein
   the conditions include a combination of spectral characteristics which minimizes errors in estimating by the pigment amount estimating section, based on the spectral characteristics of the pigments relating to the target.

5. The image processing apparatus according to claim 2, wherein the conditions include a condition for a noise characteristic of the image pickup section.

6. The image processing apparatus according to claim 1, wherein the target includes a translucent object colored with the pigments.

7. The image processing apparatus according to claim 6, wherein the target includes a biological tissue sample.

8. The image processing apparatus according to claim 7, wherein the pigments include hematoxylin and eosin.

9. The image processing apparatus according to claim 5, wherein the spectral characteristic estimating section is configured to perform Wiener estimation.

10. The image processing apparatus according to claim 6, wherein the pigment amount estimating section is configured to perform estimation according to Lambert-Beer's law.

11. The image processing apparatus according to claim 8, wherein the number of optical filters is two.

12. An image processing apparatus comprising:
    an image pickup section configured to use an image pickup element to pick up images of a target illuminated by transmission type illumination, via at least one optical filter;
    a spectral characteristic estimating section configured to estimate a spectral characteristic relating to the target for a plurality of pixels of the target based on the images picked up by the image pickup section; and
    a pigment amount estimating section configured to estimate an amount of a number of pigments relating to each of the plurality of pixels of the target based on the spectral characteristic;
    wherein the at least one optical filter has a variable transmission wavelength and a number of settings equal to the number of pigments whose amount is estimated by the pigment amount estimating section.

13. The image processing apparatus according to claim 2, wherein the estimating section is configured to estimate the amount of the pigments relating to the target for each local image area containing at least two proximate pixels.

14. The image processing apparatus according to claim 13, wherein sizes of all of the local image areas contained in a single image are equal.

15. A method for processing images, the method comprising:
    picking up images of a target illuminated by a transmission type illumination, via a number of optical filters;
    estimating a spectral characteristic relating to the target for a plurality of pixels of the target based on the picked-up images; and
    estimating an amount of a number of pigments relating to each of the plurality of pixels of the target based on the spectral characteristic;
    wherein the number of optical filters used for the image pickup is equal to the number of pigments whose amount is estimated.

16. A method for processing images, the method comprising:
    picking up images of a target dyed with a number of predetermined pigments, via a number of optical filters with different spectral characteristics;
    estimating a spectral characteristic relating to the target for a plurality of pixels of the target based on the picked-up images;
    estimating an amount of each of the pigments for each of the plurality of pixels based on the estimated spectral characteristic for each of the pixels; and
    analyzing the target based on a distribution of the estimated amounts of the pigments, wherein the number of the optical filters is equal to the number of the pigments, and a combination of the different spectral characteristics of the optical filters is preselected so as to minimize errors the amounts of pigments.

17. An image processing apparatus comprising:
    image pickup means for using an image pickup element to pick up images of a target illuminated by transmission type illumination, via a number of optical filters;
    spectral characteristic estimating means for estimating a spectral characteristic relating to the target for each of the plurality of pixels of the target based on the images picked up by the image pickup means; and
    pigment amount estimating means for estimating an amount of a number of pigments relating to the plurality of pixels of the target based on the spectral characteristic;
    wherein the number of optical filters used for the image pickup is equal to the number of pigments whose amount is estimated by the estimating means.

* * * * *